(12) United States Patent
Okada et al.

(10) Patent No.: US 7,491,518 B2
(45) Date of Patent: Feb. 17, 2009

(54) METHOD OF ELEVATING YIELD OF OLIGOSACCHARIDES CONTAINING α-GALACTOSYL AND ANTI-CANDIDA COMPOSITIONS

(75) Inventors: Masamichi Okada, Kakamigahara (JP); Shigeharu Mori, Kakamigahara (JP); Hiroyuki Hashimoto, Osaka (JP); Koki Fujita, Yokohama (JP); Kozo Hara, Yokohama (JP)

(73) Assignees: Amano Enzyme Inc., Aichi (JP); Bio Research Corporation of Yokohama, Kanagawa (JP); Ensuiko Sugar Refining Co., Ltd., Tokyo (JP)

( * ) Notice: Subject to any disclaimer, the term of this patent is extended or adjusted under 35 U.S.C. 154(b) by 675 days.

(21) Appl. No.: 10/362,483

(22) PCT Filed: Aug. 8, 2001

(86) PCT No.: PCT/JP01/06848

§ 371 (c)(1),
(2), (4) Date: Feb. 25, 2003

(87) PCT Pub. No.: WO02/18614

PCT Pub. Date: Mar. 7, 2002

(65) Prior Publication Data

US 2004/0101938 A1    May 27, 2004

(30) Foreign Application Priority Data

Aug. 30, 2000    (JP)    ............... 2000-260359

(51) Int. Cl.
C12P 19/14    (2006.01)
C12P 19/12    (2006.01)
C12P 19/18    (2006.01)

(52) U.S. Cl. .......................... 435/101; 435/97; 435/99; 435/100

(58) Field of Classification Search .................. 435/101, 435/100, 99, 97
See application file for complete search history.

(56) References Cited

U.S. PATENT DOCUMENTS 3,846,239 A * 11/1974 Delente et al. ............... 435/208
3,966,555 A *  6/1976 Arnaud et al. ............... 435/208
4,431,737 A *  2/1984 Olivieri et al. ............... 435/448
6,329,182 B1 * 12/2001 Pedersen et al. ............... 435/96

FOREIGN PATENT DOCUMENTS

EP    0 192 401    8/1986
JP    61-187787    8/1986
JP    2-84191    * 3/1990
JP    4-126087    4/1992
JP    5-23183    2/1993
JP    5-140178    6/1993
JP    5-146273    * 6/1993
JP    8-508644    9/1996
JP    11-240837    9/1999
WO    WO 94/23022    10/1994

OTHER PUBLICATIONS

Nilsson (Carb. Res. 167:95-103 (1987)).*
Vic et al (Tetrahedron: Asymmetry 7(7):1973-1984 (1996)).*
Kaneko et al. "Substrate speificity of alpha-galactosidase from *Aspergillus niger* 5-16" Agri. Biol. Chem. (1991) 55(1): 109-115.*
Manzanares et al. "Characterization of galactosidases from *Aspergillus niger*: purification of a novel alpha-galactosidase activity" Enzyme Microb. Technol. (1998) 22: 383-390.*
Brady et al. "General Chemistry: Principles and Structure" Second edition. (1978) (John Wiley and Sons: New York), pp. 328-330.*
Monsan et al. "Enzymatic synthesis of oligosaccharides" FEMS Microbiol. Rev. (1995) 16: 187-192.*
Synthesis of α-Galacto-Oligosaccharides Using Thermostable α-Galactosidase; Masaru Mitsutuomi, Shiga University, Agricultural Department; 1994; pp. 212-216.
Three α-Galactosidase Genes of *Trichoderma reesei* Cloned By Expression in Yeast; Emilio Margolles-Clark et al.; European Journal of Biochemistry; 1996; pp. 104-111.
Scigelova et al. Purification of α-galactosidase from *Aspergillus niger* for application in the sunthesis of complex oligosaccharides J. Molec. Catal. B: Enzymatic 8(2000): 175-181.
De Vries et al. Differential Expression of Three α-Galactosidase Genes and a Single β-Galactosidase Gene from *Aspergillus niger* Appl Env. Microbiol. (1999).
Manzanares et al. Characterization of galactosidases from *Aspergillus niger*: purification of a novel α-galactosidase activity Enz. Microb. Technol. (1998) 22:383-390.

* cited by examiner

*Primary Examiner*—Sandra Saucier
*Assistant Examiner*—Susan Hanley
(74) *Attorney, Agent, or Firm*—Jordan and Hamburg LLP (57) ABSTRACT

A novel method of very efficiently elevating the yield of oligosacchrides containing α-galactosyl, compared with the conventional methods, which comprises treating galactose or a galactose-containing material with a specific α-galactosidase and thus performing a dehydrocondensation reaction at a high substrate concentration. Anti-candida compositions originating in foods, having a high safety and excellent anti-candida effect and not being restricted in the supply, which contain as the active ingredient oligosacchrides obtained by treating galactose or a galactose-containing material with an α-galactosidase and thus performing a dehydrocondensation.

4 Claims, 8 Drawing Sheets

—◇— pH
——— Absorbance
—●— Activity

Figure 9

× Galactose
○ α-Galactobiose
□ α-Galactotriose
△ α-Galactotetraose or higher oligosaccharides

Figure 10

1: α-Galactotetraose or higher oligosaccharides
2: α-Galactotriose
3: α-Galactobiose

Figure 11

1: Oligosacchrides containing α-galactosyl of trisaccharide or higher
2: α-Galactosyl glucose
3: α-Galactobiose

Figure 12

× Galactose
○ α-Galactobiose
□ α-Galactotriose
△ α-Galactotetraose or higher oligosaccharides

Figure 13

Enzyme in EXAMPLE 1( ● : α-Galactobiose, ○ : α-Galactotriose)
Protease B "AMANO" (■ : α-Galactobiose, □ : α-Galactotriose)
Nuclease "AMANO" (▲ : α-Galactobiose, △ : α-Galactotriose)

Figure 14

METHOD OF ELEVATING YIELD OF OLIGOSACCHARIDES CONTAINING α-GALACTOSYL AND ANTI-CANDIDA COMPOSITIONS

FIELD OF THE INVENTION

The present invention relates to a method of elevating the yield of an oligosaccharide containing α-galactosyl by treating galactose or a galactose-containing material with a specific microorganism-derived galactosidase and an anti-candida composition comprising as an active ingredient an oligosacchride containing α-galactosyl other than raffinose.

BACKGROUND OF THE INVENTION

Recently, various saccharide-related enzymes which synthesizes certain oligosaccharides were screened for on the basis of microorganisms, and the advancement in a technology for utilizing such a microorganism-derived enzyme and in a technology for purifying a resultant synthetic oligosaccharide extensively enables a large scale production of the oligosaccharide at a low cost. Accordingly, an oligosaccharide became utilizable even in a field familiar to us such as a food industry. Those known typically are a coupling sugar, fractooligosaccharide, β-galactooligosaccharide, soybean oligosaccharide, isomaltooligosaccharide, palatinose, lactosucrose oligosaccharide and the like.

Any of these oligosaccharide was reported to have a bifidus microorganism growth activity or a cariostatic or anti-cariogenic property as well as a mineral absorption-promoting effect, and is utilized as a specified health-care food or a starting material thereof.

It is also reported recently that an oligosaccharide containing α-galactosyl such as melibiose, manninotriose, raffinose and stachyose has a potent proliferating effect on a bifidus microorganism, has a favorable property as a food, and have a carcinostatic effect or natural killer cell-activating effect (Shigeki Motoi et al, Japanese Cancer Association (meeting report), 40, 132 (1981)), and such an oligosaccharide is considered to be extremely useful and attractive as a beverage, food product, pharmaceutical and a starting material thereof.

A known source of raffinose is a beet or soybean oligosaccharide, while that of stachyose is a soybean oligosaccharide. However, a soybean oligosaccharide is not found in abundance, and can not be supplied in a large amount. Besides, it is costly. Raffinose contained in a beet is also disadvantageous since it is available only during a period of October to March, its annual supply is only several 100 tons and its current price is so high. Melibiose and manninotriose are present in small amounts in a soybean oligosaccharide, and have the structures formed by deleting a fructose moiety from raffinose and stachyose, respectively. While they are synthesized artificially by means of the decomposition of raffinose and stachyose, they are very expensive since the starting raffinose and stachyose are also expensive.

On the other hand, an enzyme reaction employing an α-galactosidase may also be employed for synthesizing an oligosaccharide containing α-galactosyl. Such an enzyme reaction is classified into a saccharide transfer reaction and a dehydrocondensation reaction.

The saccharide transfer reaction is not suitable as an industrial method since it requires a synthesis substrate such as p-nitrophenyl α-galactoside as an α-galactosyl group donor (JP-A-10-201472) and also requires as a substrate an expensive compound containing α-galactosyl such as raffinose.

When utilizing the dehydrocondensation reaction, it is possible to conduct a reaction at a high substrate concentration, and a free galactose employed as a substrate may be one obtained by a hydrolysis of a less expensive saccharide such as lactose, whereby accomplishing an economically advantageous reaction.

An enzyme which can be employed in this dehydrocondensation reaction is proposed to be an α-galactosidase produced by a microorganism such as *Pycnoporus cinnabarinus*, *Streptococcus bovis*, *Diplococcus pneumoniae*, *Mortierella vinacea*, *Pseudomonas fluorescens* strain H-601 (deposition No: FERM P-11027) and *Candida guilliermondii* strain H-404 (deposition No: FERM P-11026) as well as a plant such as *Vicia sativa* and Green coffee bean (Japanese Patent No. 3028258).

However, these enzymes are not applied to an industrial scale production since they exhibit low reaction rates and low reaction yields at high substrate concentrations. Thus, the α-galactosidase produced by *Candida guilliermondii* strain H-404 which has been believed to exhibit the highest reaction rate and the highest reaction yield requires a period, for example, as long as about 90 hours until its reaction is plateaued when being treated with 60% (w/v) galactose under the conditions of 35 $U^M$/g-galactose and 50° C., but only gives an yield of oligosacchrides containing α-galactosyl as low as about 25% (Applied Science of *Saccharide*, 44, 69-75, 1997).

As described above, an oligosaccharide containing α-galactosyl having useful characteristics as a food material is not supplied in a large amount or at a low cost and desired to be produced on an industrial scale.

The invention is intended to solve the problem that a conventional method poses a low reaction rate and a low reaction yield in a dehydrocondensation reaction at a high substrate concentration and is less practical, and its objective is to provide a method for producing an oligosaccharide containing α-galactosyl far more efficiently than any conventional method by using a certain α-galactosidase.

On the other hand, a *Candida* microorganism is one of the yeasts which are persistent in the intestine of a human, and is an opportunistic pathogen inducing a serious systemic infections when the resistance is reduced due to an infectious disease or other diseases. An intestinal *Candida* microorganism exerts its effect on an immune system via the cell itself or a *Candida* toxin produced by the microorganism, and was reported to serve as an atopic dermatitis exacerbation factor (Michio Matsuda et al., allergy clinics, 56, 768-772 (1991)) or to be involved in the allergic diseases other than the atopic dermatitis, such as bronchial asthma and rhinitis. Otherwise, it induces, when proliferating abnormally in an intestine, a health problem such as a chronic fatigue called yeast connection, headache, uneasiness, unsettledness, depression and the like.

As a method for treating such a *Candida*-induced mycosis or atopic dermatitis, an antifungal therapy is considered to be effective, and it was reported recently that a trisaccharide raffinose occurring in a beet plant has not only in vitro but also in vivo inhibitory and eradicative effects on a *Candida* microorganism (JP-A-11-240837) and actually exerted an effect on an atopic dermatitis (Taizo Nagura et al, Food Industries, 2.28, 29, 1999). An oral administration of raffinose does not cause side effects observed with an antifungal agent such as a transient exacerbation of rash or digestive organ signs, and is regarded as a safer therapy against an atopic dermatitis.

Nevertheless, a further potent and further safer therapy has been demanded since the anti-candida effect of raffinose is lower than that of an antifungal agent. Also since a *Candida* microorganism has various adverse effects on a human health as described above, a food product having a more potent anti-candida effect has been desired from a viewpoint of a diet-based health control trend in response to the demand of reducing the medical expense. Another problem associated with raffinose is its limited supply and expensiveness as described above.

On the other hand, the physiological functions of an oligosaccharide containing α-galactosyl other than raffinose were also reported intensively, including a neutralizing effect of α-1,3-galactobiose (α-1,3 Gal2) on a toxin produced by *Clostridium difficile* which is a causative bacteria of a colitis (L. D. Heerze et al., J.Infect.Dis, 169, 1291-1296 (1994)) and an inhibitory and therapeutic effect of α-1,4 galactobiose (α-1,4 Gal2) on a pathogenic *E.coli* 0157 (C. A. Lingwood, Adv. Lipid Res., 25, 189-211 (1993)).

Nevertheless, no reports suggested any anti-candida effect of an oligosaccharide containing α-galactosyl other than raffinose.

Also since α-galactosyl group is present only in the form of an α-galactobiose (α-Gal2) in a living body and the α-1,6-galactosyl glucose structure possessed by raffinose does not exist while the mechanisms of the anti-candida effect of raffinose are considered to be based on the intestinal flora-improving effect, the inhibitory effect on the adhesion or settlement of a *Candida* microorganism on a digestive tract and the immune activation effect, we assumed that α-Gal2 plays an important role in the in vivo effect of raffinose and focused on an oligosaccharide containing α-galactosyl other than raffinose, whereby accomplishing the invention.

Accordingly, an objective of the invention is to provide an anti-candida composition which is derived from a food, highly safe, excellent in anti-candida effect, and can be supplied limitlessly.

SUMMARY OF THE INVENTION

The invention relates to a method of elevating the yield of an oligosaccharide containing α-galactosyl comprising treating galactose or a galactose-containing material with an α-galactosidase derived from a specific microorganism, and such an microorganism which produces an α-galactosidase employed in the invention may, for example, be a fungus such as *Aspergillus*, *Penicillium* and *Trichoderma*, yeast such as *Saccharomyces* and a bacterium such as *Bacillus*, with an α-galactosidase derived from a microorganism of *Aspergillus* being preferred.

Among the microorganisms listed above, those employed preferably are *Aspergillus niger*, *Aspergillus oryzae* and *Aspergillus pulverulentus* among the fungi of *Aspergillus*, *Penicillium citrinum* and *Penicillium multicolor* among the fungi of *Penicillium* and *Trichoderma viride* among the fungi of *Trichoderma*, with *Aspergillus niger* being preferred especially.

*Saccharomyces cerevisiae* is preferred among the yeasts of *Saccharomyces*, and *Bacillus megaterium* is preferred among the bacteria of *Bacillus*.

Moreover, it was also discovered that a fungus we isolated from a soil produces a novel α-galactosidase which is utilizable in the invention.

This strain has the following mycological characteristics.
Conidial top: Spherical to radial.
Conidium (optical microscope): Spherical to semi-spherical, smooth to slightly rough surface.
Conidium (electron microscope): Rough surface (protrusion), diameter (about 3.5 to 4.0 μm).
Exudate: Slight (transparent to tan).
Odor: Almost none
Sterigmata: 2-Stage.
Colony formation rate (malt extract agar medium, incubated at 25° C.): >85 mm (7-day incubation), >85 mm (12-day incubation).
Colony growth rate (Czapek's yeast agar medium, incubated at 25° C.): 60 to 67 mm (7-day incubation), 65 to 73 mm (12-day incubation).
Colony color (malt extract agar medium): Black (front), colorless (back)
Colony color (Czapek's yeast agar medium): Black to grayish black (front), cream to grayish yellow (back)

This strain is classified as *Aspergillus niger ver. niger* based on the conidial shape, sterigmata and colony color. We designated this strain as *Aspergillus niger* strain APC-9319. This strain was deposited under the deposition number of FERM BP-7680 to International Patent Organism Depositary of National Institute of Advanced Industrial Science and Technology (IPOD) (transfer from domestic deposition to international deposition, Original deposition date: Aug. 29, 2000, Domestic deposition number: FERM P-18003).

This novel α-galactosidase has the following physicochemical characteristics:

[1] Effect

It catalyzes a reaction for hydrolyzing an α-galactoside bond to liberate D-galactose:

Gal1α-OR+H$_2$O->Gal-OH+R—OH wherein Gal1α-OR is a saccharide containing α-galactosyl, Gal-OH is a free galactose, and R—OH is a compound containing hydroxyl such as various saccharides, alcohols and phenols);

[2] Substrate Specificity

It acts on a saccharide having an α-galactosyl group at its non-reducing terminal such as melibiose, raffinose and stachyose as well as p-nitrophenyl α-galactoside, with the relative rate at which melibiose is decomposed being about 9 based on the decomposition rate using p-nitrophenyl α-galactoside as a substrate being regarded as 100;

[3] Optimum pH and pH Stability

Its optimum pH is 2.5 to 6.0, and it is stable within the range from pH 3.5 to 8.0 when allowed to stand for 1 hour at 40° C.;

[4] Optimum Temperature and Heat Stability

Its optimum temperature at pH 4.5 (acetate buffer) is 60° C., and it is stable at a temperature not higher than 60° C. when allowed to stand at pH 4.5 (acetate buffer) for 15 minutes;

[5] Molecular Weight and Isoelectric Point

Its molecular weight measured by a gel filtration method using a YMC-Pack Diol-200 column (YMC) is 217,000 and its molecular weight measured by an SDS-PAGE is 117,000, while its isoelectric point measured by an isoelectric focusing is 4.2.

When producing an α-galactosidase using any of these microorganisms, a solid culture or liquid culture is usually employed.

A medium for a solid culture is a wheat bran itself or a wheat bran supplemented with various additives including organic and inorganic nitrogen compounds, such as KINAKO powder, soybean powder, ammonium salt, nitrate, urea, glutamic acid, aspartic acid, polypeptone, corn steep liquor, meat extract, yeast extract, protein hydrolysate and the like. In addition, suitable inorganic salts may also be added.

A medium for a liquid culture may for example be a synthetic medium or natural medium containing carbon sources, nitrogen sources, inorganic salts and essential nutritions which are required for a favorable growth of a relevant microorganism and a satisfactory production of an enzyme. For example, a carbon source may be a carbohydrate such as a starch or constituent thereof, roasted dextrin, processed starch, starch derivative, physically processed starch and a starch or a galactose-containing material. Typically, a soluble starch, corn starch, potato starch, sweet potato starch, dextrin, amylopectin, amylose, galactose, lactose, raffinose, and the like, any of which can be employed alone or in combination with each other.

A nitrogen source may for example be an organic nitrogen source material such as a polypeptone, casein, meat extract, yeast extract, corn steep liquor or soybean extract or soybean lee extract, an inorganic salt nitrogen compound such as ammonium sulfate and ammonium phosphate, and an amino acid such as glutamic acid, any of which can be employed alone or in combination with each other.

An inorganic salt may for example be a phosphate such as monopotassium phosphate and dipotassium phosphate, a magnesium salt such as magnesium sulfate, a calcium salt such as calcium chloride and a sodium salt such as sodium carbonate, any of which can be employed alone or in combination with each other.

A solid culture is conducted without shaking at a pH of the culture medium within the range from 3 to 7, preferably 4 to 7, to which an inventive microorganism is inoculated and cultured at 10 to 40° C., preferably 20 to 37° C. for 1 to 10 days. After incubation, the culture medium extract was subjected to an ethanol precipitation and the like to obtain α-galactosidase as a crude enzyme precipitate.

A liquid culture is conducted with shaking or with aerating and stirring under an aerobic condition, at a pH of the culture medium within the range from 4 to 10, preferably 5 to 8 at a temperature of 10 to 40° C., preferably 25 to 37° C., for a period of 24 to 96 hours. After incubation, the cells were removed by centrifugation or other suitable solid-liquid separation means to obtain a culture supernatant. Alternatively, the cells were treated physically or enzymatically to obtain an intracellular extract.

Then, such a crude enzyme solution is subjected to a suitable combination of an ammonium sulfate salting out, gel filtration, hydrophobic interaction chromatography and the like to obtain a highly pure α-galactosidase.

An enzyme used for producing an oligosaccharide containing α-galactosyl may not only be the enzyme preparations obtained by the above-described method but also an extract of a solid culture and a culture supernatant or intracellular extract of a liquid culture which may be employed as enzyme formulations as they are. If necessary, an enzyme obtained by a known purification method may also be employed. It is also possible to use a cell itself as an enzyme formulation. Otherwise, an α-galactosidase present as a contaminant in a commercially available enzyme formulation, such as a cellulase or protease formulation may also be employed, and in such a case the enzyme formulation may be used as it is or subjected to a known purification process to isolate the intended α-galactosidase.

Examples of the commercially available enzyme formulation products employed for producing an oligosaccharide containing α-galactosyl are listed below: *Aspergillus niger*-derived α-Galactosidase S-DS (6,500 U/g), lipase A "AMANO" 6 (231 U/g), hemicellulase "AMANO" 90G (97 U/g) or cellulase A "AMANO" 3 (26 U/g), *Aspergillus oryzae*-derived "UMAMIZYME" (163 U/g), protease M "AMANO" (3 U/g), *Aspergillus pulverulentus*-derived pectidase G "AMANO" (131 U/g), *Penicillium citrinum*-derived protease B "AMANO" (235 U/g) or nuclease "AMANO" (388 U/g), *Trichoderma viride*-derived cellulase "AMANO" 4 (6 U/g) and the like.

Among those listed above, *Aspergillus niger*-derived α-Galactosidase S-DS (6,500 U/g), *Penicillium citrinum*-derived protease B "AMANO" (235 U/g) and nuclease "AMANO" (388 U/g) are preferred.

All of the commercially available enzyme formulations described above are the products by AMANO ENZYME, and the number of each trade name represents the activity level of the α-galactosidase contained. The activity was measured by the method in Reference Example 1 described below using an acetate buffer, pH6.0.

Such an enzyme or a cell which produces such an enzyme can be immobilized and utilized repetitively in the reaction in a continuous or batch process.

A starting material to be subjected to an α-galactosidase reaction may for example be galactose or a galactose-containing material. Those exemplified typically are galactose, a mixture of galactose and glucose, a hydrolysate of a galactose-containing compound such as lactose and the like, any of which can be employed alone or in combination with each other. The galactose is not only a commercially available galactose but also a galactose obtained by hydrolyzing a naturally occurring or synthetic oligosaccharide containing α-galactosyl or β-galactosyl, glucoside or polysaccharide such as melibiose, manninotriose, raffinose, stachyose, planteose, verbascose, galactans, galactomannan, arabinogalactan, rhamnogalactan, galactolipid, ferulated galactose, galactopinitol, galactosylglycerol, galactinol, lactose, lactitol, lactulose, galactooligosaccharide and the like with an enzyme (β-galactanase, β-galactosidase, α-galactosidase and the like) or an acid.

The ratio of galactose and glucose in the mixture is not limited particularly, as far as galactose is contained.

Glucose, which is to be combined with galactose, is not only a commercially available glucose but also a glucose obtained by hydrolyzing a naturally occurring or synthetic oligosaccharide containing α-glucosyl or β-glucosyl, glucoside or polysaccharide such as starch, maltooligosaccharide, isomaltooligosaccharide, nigerooligosaccharide, kojic oligosaccharide, cyclodextrin, trehalose, maltitol, cellulose, cellooligosaccharid, sophorooligosaccharide, laminaologosaccharide, gentiooligosaccharide and the like with an enzyme (amylase, glucoamylase, cellulase, α-glucosidase, β-glucosidase and the like) or an acid. The compound which is to be combined with galactose is not limited to glucose, and may be any other saccharide.

As a hydrolysate of a compound containing galactose, a material obtained by hydrolyzing a naturally occurring or synthetic oligosaccharide containing α-galactosyl or β-galactosyl, glucoside or polysaccharide such as melibiose, manninotriose, raffinose, stachyose, planteose, verbascose, galactans, galactomannan, arabinogalactan, rhamnogalactan, galactolipid, ferulated galactose, galactopinitol, galactosylglycerol, galactinol, lactose, lactitol, lactulose, galactooligosaccharide and the like with an enzyme (β-galactanase, β-galactosidase, α-galactosidase and the like) or an acid can be utilized as it is. Among those listed above, a lactose hydrolysate obtained by hydrolyzing a less expensive lactose with β-galactosidase or an acid is utilized preferably as it is. In addition, a lactose hydrolysate may be supplemented with galactose or glucose described above, or its ratio between galactose and glucose can be changed using an ion exchange chromatography, an activated charcoal column and the like.

While an α-galactosidase is a hydrolytic enzyme naturally, it catalyzes a dehydrocondensation reaction, which is a reverse reaction of the hydrolysis, at an elevated level of galactose as a starting material which serves as a substrate. Accordingly, when galactose at a high level is treated with an α-galactosidase, oligosacchrides containing α-galactosyl which are compositions consisting of various oligosaccharides such as disaccharides, trisaccharides and tetrasaccharides having a structure represented by α-(Gal)n (wherein n is usually an integer of 2 to 10, Gal is galactose) are formed. The site where an α-galactosyl group is bound at the non-reducing terminal of such an oligosaccharide containing α-galactosyl is exemplified below.

[1] α-(Gal)n containing an α-1,6-galactosyl group at the non-reducing terminal (wherein n is usually an integer of 2 to 10).

[2] α-(Gal)n containing an α-1,3-galactosyl group at the non-reducing terminal (wherein n is usually an integer of 2 to 10).

[3] α-(Gal)n containing an α-1,2-galactosyl group at the non-reducing terminal (wherein n is usually an integer of 2 to 10).

[4] α-(Gal)n containing an α-1,4-galactosyl group at the non-reducing terminal (wherein n is usually an integer of 2 to 10).

The number of the bindings (n) is preferably 2 to 8, more preferably 2 to 6.

When glucose is present in the reaction system, an oligosaccharide containing α-galactosyl having a structure represented by α-(Gal)n-Glc (wherein n is usually an integer of 1 to 9, Glc is glucose) resulting from the binding between galactose and glucose is formed in addition to an oligosaccharide having a structure represented by α-(Gal)n. The site where an α-galactosyl group is bound at the non-reducing terminal of such an oligosaccharide containing α-galactosyl is exemplified below.

[5] α-(Gal)n-Glc containing an α-1,6-galactosyl group at the non-reducing terminal (wherein n is usually an integer of 1 to 9).

[6] α-(Gal)n-Glc containing an α-1,3-galactosyl group at the non-reducing terminal (wherein n is usually an integer of 1 to 9).

[7] α-(Gal)n-Glc containing an α-1,2-galactosyl group at the non-reducing terminal (wherein n is usually an integer of 1 to 9).

[8] α-(Gal)n-Glc containing an α-1,4-galactosyl group at the non-reducing terminal (wherein n is usually an integer of 1 to 9).

The number of the bindings (n) is preferably 1 to 8, more preferably 1 to 6.

In the procedure described above, the separation of an oligosaccharide from an enzyme reaction solution after completion of the reaction can be accomplished by a known separation means such as an ion exchange chromatography, activated charcoal column chromatography, gel filtration column chromatography and the like.

Since the advancement of an enzyme reaction is accompanied with a saccharide transfer reaction due to the α-galactosidase-catalyzed re-decomposition of an oligosaccharide ontaining α-galactosyl which was synthesized previously by a dehydrocondensation reaction, the saccharide transfer reaction also contributes to the synthesis of the oligosacchride containing α-galactosyl.

The site and the number of the binding of galactose in a resultant compound or the ratio of such a compound may vary depending on the ratio between galactose and glucose in the starting material, origin of the enzyme employed or reaction conditions.

While the condition under which an α-galactosidase is reacted may vary depending on the enzyme employed, the reaction pH is 3.0 to 10.0, preferably 4.0 to 9.0.

The reaction temperature is preferably high in view of the solubility and the reaction rate, and usually 20 to 90° C., preferably 40 to 80° C. The reaction time may vary depending on the mount of an enzyme employed, and is usually 1 to 150 hours. Nevertheless, the invention is not limited to the conditions or reaction modes described above.

When an oligosacchride ontaining α-galactosyl of the invention is produced, a higher concentration of galactose as a starting material is more preferred, and galactose or glucose may precipitate in the reaction system, or be present in a supersaturated condition, and used as a concentration usually of 5 to 110% (w/v), preferably 40 to 110% (w/v).

For the purpose of an efficient production of an oligosacchride containing α-galactosyl by elevating galactose concentration substantially, galactose is treated with an α-galactosidase to effect a dehydrocondensation reaction as a preliminary reaction and thereafter the reaction solution is concentrated under reduced pressure prior to the dehydrocondensation reaction as a main reaction. This reaction here may be conducted in a system separate from the preliminary reaction by isolating the concentrated solution, or may be conducted in the preliminary reaction system without isolating the concentrated solution.

When the level of galactose is elevated at the stage of the initial charging, galactose undergoes precipitation, which may lead to a reduction in the yield of an oligosaccharide containing α-galactosyl. Nevertheless, the inventive method in which the galactose level is elevated substantially to effect a dehydrocondensation reaction as described above prevents any precipitation of galactose or any inactivation of the enzyme due to the foaming upon concentration and promotes the dehydrocondensation reaction markedly, thus allowing an oligosacchride containing α-galactosyl to be produced efficiently within a short period of time at a high yield. An enzyme employed in this production method is preferably one having a higher catalytic activity of the dehydrocondensation reaction, such as those derived from various microorganisms employed in an inventive yield elevating method among which the α-galactosidase obtained from *Aspergillus niger* strain APC-9319 (FERM BP-7680) is particularly preferred and can produce an oligosaccharide containing α-galactosyl efficiently. The concentration under reduced pressure can be accomplished by any known means for concentration under reduced pressure such as a rotary evaporator and a vacuum crystallization container The invention also relates to an anti-*Candida* composition comprising as an active ingredient an oligosaccharide containing α-galactosyl other than raffinose which is synthesized by treating galactose or a galactose-containing material with an α-galactosidase followed by a dehydrocondensation reaction.

While the origin or type of a microorganism which produces an α-galactosidase employed for synthesizing an oligosaccharide containing α-galactosyl of the invention is not limited particularly, and may be one derived from a plant such as a green coffee, any of various α-galactosidases derived from the microorganisms employed in an inventive yield elevating method, especially an αgalactosidase derived from *Aspergillus niger* strain APC-9319 (FERM BP-7680), serves to elevate the yield of the oligosaccharide containing α-galactosyl, whereby enabling a stable and less expensive supply of a food-derived highly safe anti-*Candida* composition. In addition, the synthesis may be accomplished also by treating the galactose described above with an α-galactosidases to effect a dehydrocondensation reaction as a preliminary reaction followed by concentrating the reaction solution under reduced pressure prior to the dehydrocondensation reaction as a main reaction.

An oligosacchride containing α-galactosyl of the invention may be an oligosacccharide represented by α-(Gal)n (wherein n is usually an integer of 2 to 10, Gal is galactose) consisting only of galactose or an oligosaccharide represented by α-(Gal)n-Glc (wherein n is usually an integer of 1 to 9, Glc is glucose) consisting of other saccharide except for raffinose, such as galactose and glucose.

An anti-*Candida* composition of the invention can be employed as a solid, semi-solid or liquid formed by combining an oligosacchride containing α-galactosyl other than raffinose with a customary inorganic or organic carrier or excipient. While an ordinary administration mode is an oral administration, a parenteral dosage form such as a dermal formulation can also be employed. An oral dosage form may be various formulations such as powder, granule, tablet, capsule, syrup and the like, and the formulation may contain pharmaceutically acceptable known additives such as an excipient, stability, binder, lubricant, disintegrant, suspending agent, solubilizer, flavor, sweetener and the like.

The dose of an anti-*Candida* composition of the invention is usually 1 to 15 g per day, preferably 3 to 15 g per day as an oligosaccharide containing α-galactosyl as an active ingredient when given orally to an adult. Since the oligosaccharide containing α-galactosyl as an active ingredient is produced from a material consumed as a food by a method applied to a food product and has no problem toxicologically and exhibited no acute toxicity in rats when given orally at 5000 mg per kg of body weight, its dose may be increased or decreased as appropriate depending on the condition, age, body weight, dosage form, administration mode and the like.

An anti-*Candida* composition of the invention can be applied to a mammal other than human such as cattle and horse as well as a laboratory animal such as rat and mouse, to which an oligosaccharide containing α-galactosyl whose purity is lower may also be given.

BEST MODE FOR CARRYING OUT THE INVENTION

REFERENCE EXAMPLE 1

Measurement of Activity of α-galactosidase Using p-nitrophenyl α-galactoside as Substrate 0.2 ml of 10 mM p-nitrophenyl α-galactoside and 0.2 ml of a predetermined 40 mM buffer (pH in accordance with the optimum pH of the enzyme) were combined with 0.05 ml of an α-galactosidase solution and reacted at 40° C. for 10 minutes. After reaction, 0.5 ml of 0.2 M sodium carbonate was added to terminate the reaction, and the liberated p-nitrophenol was assayed by measuring the absorbance at 400 nm using a spectrophotometer.

One enzyme activity unit (U) was defined as the level of the enzyme capable of liberating 1 micromole of p-nitrophenol within 1 minute under the condition described above.

REFERENCE EXAMPLE 2

Measurement of Activity of α-galactosidase Using Melibiose as Substrate 0.2 ml of 10 mM melibiose and 0.2 ml of a predetermined 40 mM buffer (pH in accordance with the optimum pH of the enzyme) were combined with 0.05 ml of an α-galactosidase solution and reacted at 40° C. for 10 minutes. Then the mixture was heated at 100° C. for 10 minutes to terminate the reaction, and the resultant glucose level was quantified using an F-kit manufactured by ROCHE-DIAGNOSTICS (glucose/fructose) or a high pressure liquid chromatography (HPLC).

One enzyme activity unit ($U^M$) was defined as the level of the enzyme capable of producing 1 micromole of glucose within 1 minute under the condition described above.

EXAMPLE 1

Preparation of α-galactosidase 90 ml of a liquid medium (pH6.0) containing 5% wheat bran was placed in a 500 ml Sakaguchi flask, sterilized by a standard method, inoculated with *Aspergillus niger* strain APC-9319 (FERM BP-7680) and pre-incubated (seed incubation) at 25° C. for 3 days. 500 g of the bran was combined with 400 ml of water, sterilized, inoculated with 10 ml of the pre-incubated culture, stirred thoroughly, and subjected to a main incubation at 25° C. for 4 days.

After incubation, the bran malt (koji) was pulverized, combined with 8 L of water to extract overnight at 4° C., filtered through a filter paper to obtain an extract filtrate. The resultant extract filtrate was examined for the α-galactosidase activity, which was revealed to be 3 U in 1 ml of the extract filtrate. 6 L of the extract filtrate was concentrated to 1 L using an ultrafiltration membrane (SIP manufactured by ASAHI KASEI), and combined with ammonium sulfate at a concentration giving a 70% saturation, whereby effecting a salting out.

Subsequently, the precipitate was collected by a centrifugation, dissolved in 500 ml of water, concentrated to 100 ml using an ultrafiltration membrane, combined further with 500 ml of water, concentrated to 100 ml, this procedure being repeated 3 times, whereby effecting a desalting. After desalting followed by a lyophilization, a freeze-dried powder (250 U/g) was obtained.

The extract filtrate obtained by the above-described method was combined with ammonium sulfate at a concentration giving a 70% saturation, stirred, and allowed to stand overnight at 4° C. The precipitate was collected by a centrifugation, dissolved in 10 mM phosphate buffer (pH6.0), concentrated using an ultrafiltration membrane (SIP manufactured by ASAHI KASEI), combined again with the same buffer solution, and then concentrated. This procedure was repeated three times, whereby effecting a desalting.

Then, an ion exchange column chromatography was conducted using a DEAE-TOYOPEARL 650 M (TOSO) equilibrated with the same buffer solution. Subsequently, a hydrophobic interaction chromatography was conducted using a butyl-TOYOPERAL 650 M (TOSO) column in 50%-saturated ammonium sulfate.

The active fractions were collected, and subjected to a gel filtration column chromatography using a TOYOPERAL HW-55S (TOSO) column equilibrated with 50 mM acetate buffer (pH5.5) containing 0.3M sodium chloride.

As a result of these column chromatographies, an α-galactosidase whose proteins are homogeneous was obtained.

The α-galactosidase obtained as described above is an enzyme which catalyzes the reaction shown below by which a α-galactoside bond is hydrolyzed to liberate galactose.

Gal1α-OR+H$_2$O->Gal-OH+R—OH wherein Gal1α-OR is a saccharide containing α-galactosyl, Gal-OH is a free galactose, and R—OH is a compound containing hydroxyl such as various saccharides, alcohols and phenols.

Then, this enzyme was employed to measure the optimum pH and the pH stability.

Figure 1:
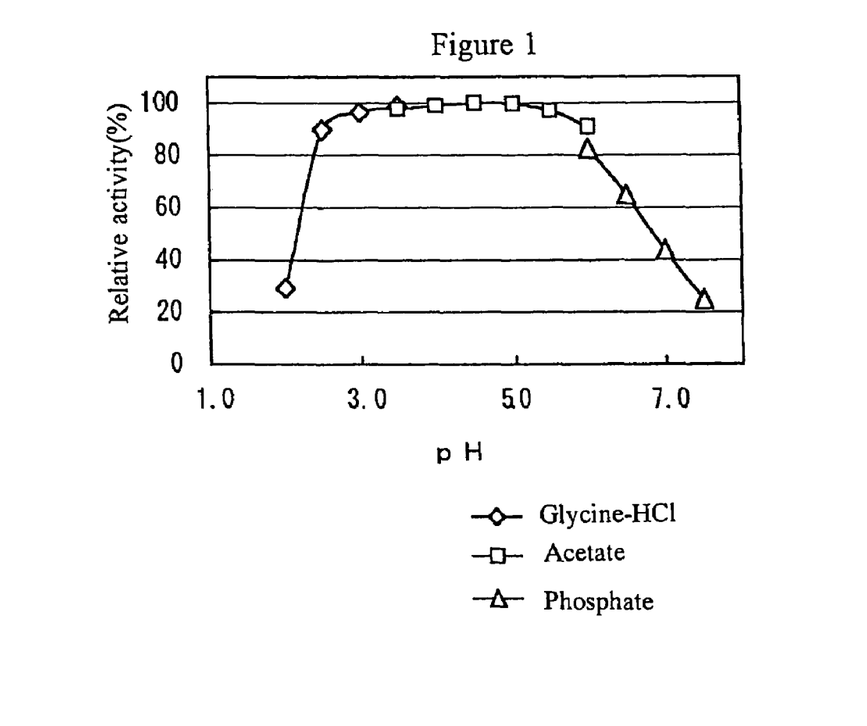
FIG. 1 shows the action pH and the optimum pH of the α-galactosidase obtained in EXAMPLE 1.
Figure 2:
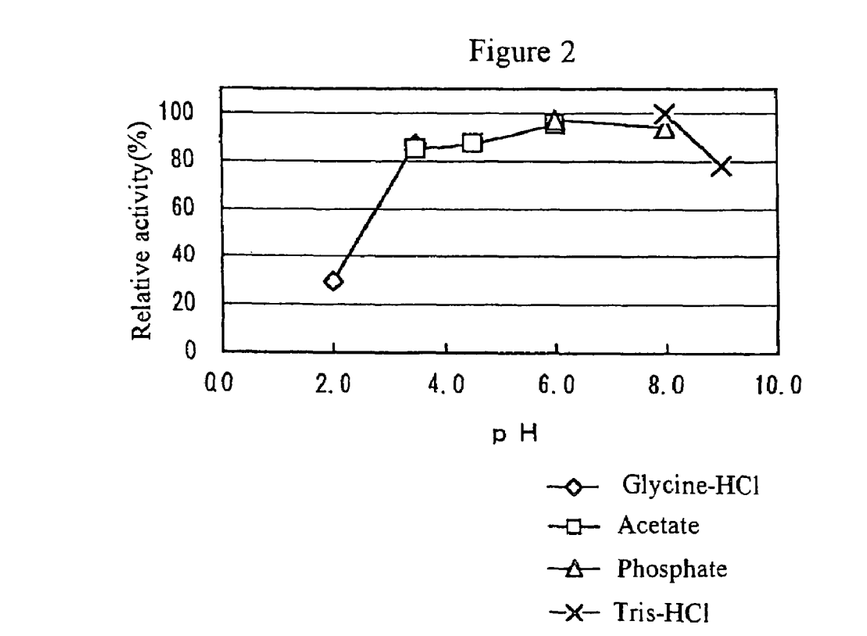
FIG. 2 shows the pH stability of the α-galactosidase obtained in EXAMPLE 1.

The enzyme activity in FIG. 1 is measured at 40° C. for 10 minutes using various buffer solutions (pH2.0 to 3.5: glycine-HCl buffer, pH3.5 to 6.0: acetate buffer, pH6.0 to 7.5: phosphate buffer). The enzyme activity in FIG. 2 is measured as a residual activity after allowing the samples to stand at 40° C. for 1 hour using various buffer solutions (pH2.5 to 3.5: glycine-HCl buffer, pH3.5 to 6.0: acetate buffer, pH6.0 to 8.0: phosphate buffer, pH8.0 to 9.0: Tris-HCl buffer). As a result, the optimum pH of this enzyme was 2.5 to 6.0, and the stability was observed within the range from 3.5 to 8.0 when allowed to stand at 40° C. for 1 hour.

The optimum temperature and the thermostability of this enzyme were also measured.

Figure 3:
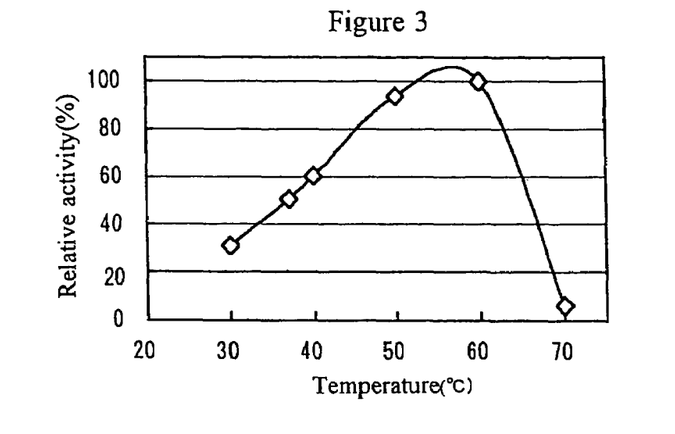
FIG. 3 shows the action temperature and the optimum temperature of the α-galactosidase obtained in EXAMPLE 1.
Figure 4:
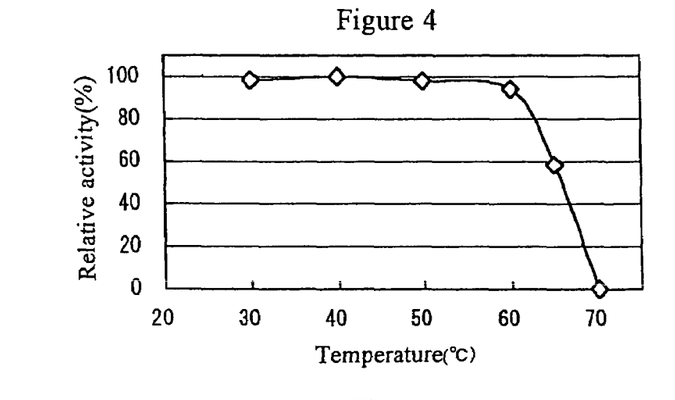
FIG. 4 shows the thermostability of the α-galactosidase obtained in EXAMPLE 1.

In FIG. 3, the enzyme activity was measured at each temperature using an acetate buffer (pH4.5). In FIG. 4, the residual activity after treating at each temperature for 15 minutes was measured using the acetate buffer (pH4.5). As a result, the optimum temperature was 60° C., and the stability was observed at 60° C. or below when allowed to stand for 15 minutes.

Figure 5:
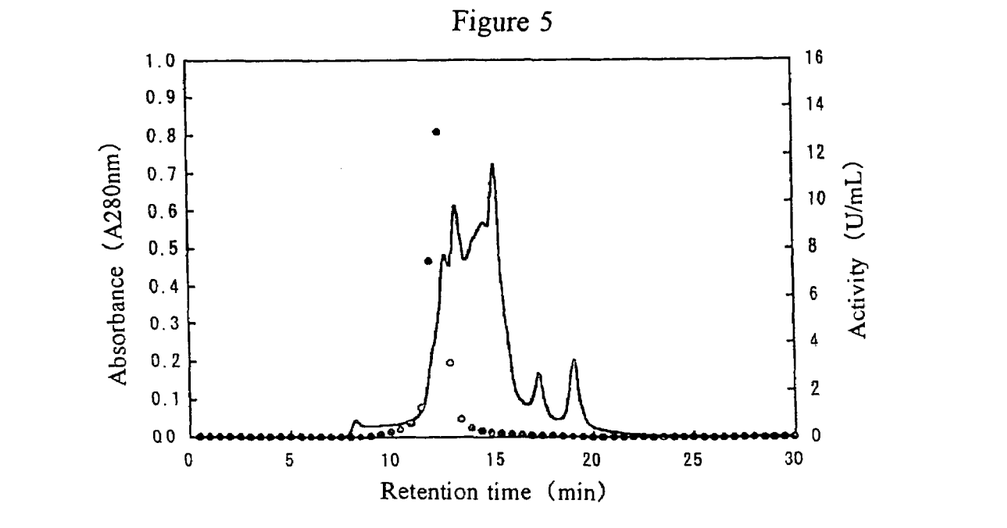
FIG. 5 shows the results of the measurement of the molecular weight of the α-galactosidase obtained in EXAMPLE 1 measured by an HPLC.
Figure 6:
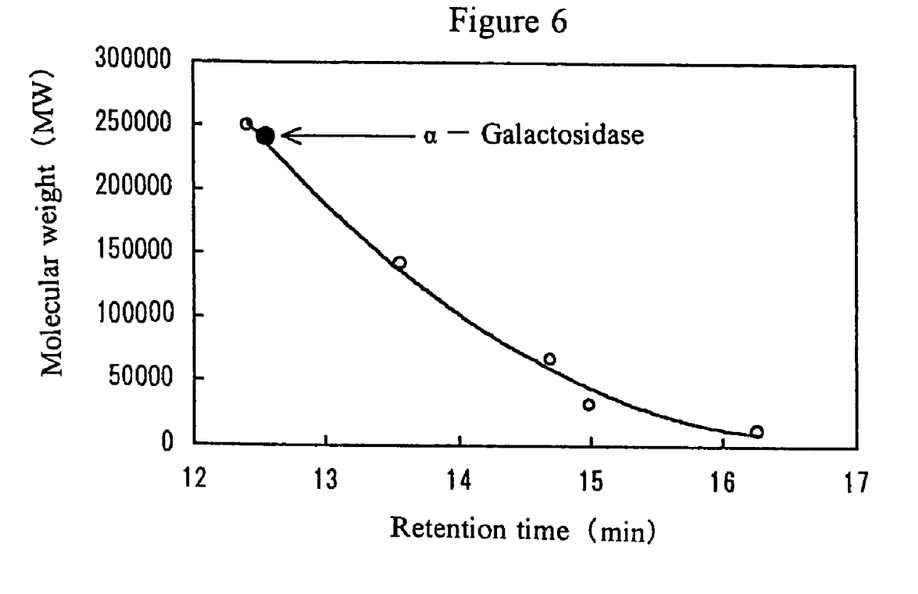
FIG. 6 shows the calibration curve in the measurement of the molecular weight of the α-galactosidase obtained in EXAMPLE 1 by an HPLC.

The molecular weight of this enzyme was determined by an HPLC. Using an HPLC column YMC-Pack Diol-200 produced by YMC equilibrated with a 0.1M phosphate buffer solution (pH7.0) containing 0.2M sodium chloride together with an MW-Marker (HPLC) produced by Oriental Yeast as a standard protein, the molecular weight was determined. In FIG. 5, the solid line represents the absorption of the protein at 280 nm, while ● represents the activity of the α-galactosidase. FIG. 6 shows a calibration curve, the standard proteins employed for which are glutamate dehydrogenase (250,000), lactate dehydrogenase (142,000), enolase (67,000), adenylate kinase (32,000) and cytochrome C (12,000) in the order of the larger molecular weight.

The figure in each bracket represents the respective molecular weight. As a result, the molecular weight of this enzyme was 217,000.

Figure 7:
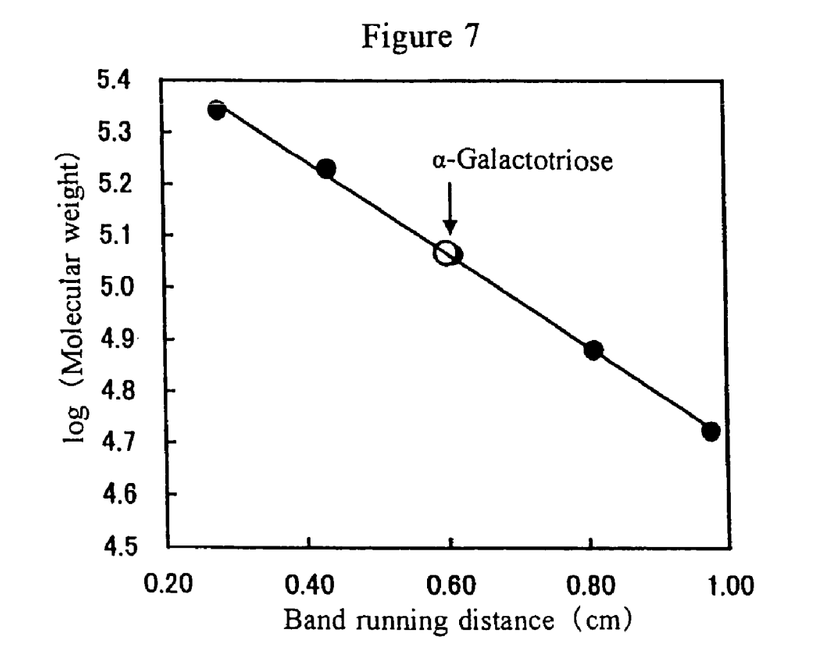
FIG. 7 shows the results of the measurement of the molecular weight of the α-galactosidase obtained in EXAMPLE 1 measured by a SDS-PAGE.

The molecular weight of this enzyme was determined also by an SDS-PAGE. The electrophoresis instrument employed was Phast System produced by Amarsham Pharmacia Biotech. The gel employed was PhastGelHomogeneous 12.5. The molecular weight markers employed were of a HMW marker kit (Amarsham Pharmacia Biotech). The standard proteins in the kit shown in FIG. 7 were myosin (220,000), α-2-macriglobulin (170,000), β-galactosidase (116,000), transferrin (76,000) and glutamate dehydrogenase (53,000) in the order of the larger molecular weight. The figure in each bracket represents the respective molecular weight. As a result, the molecular weight of this enzyme was 117,000.

Figure 8:
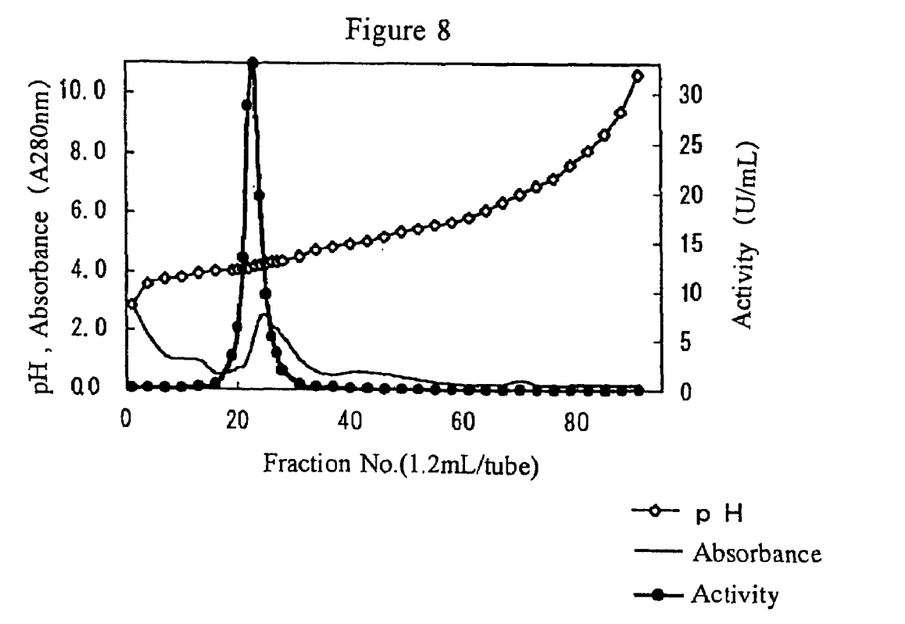
FIG. 8 shows the isoelectric point, according to the isoelectric focusing, of the α-galactosidase obtained in EXAMPLE 1.

The isoelectric point of this enzyme was determined by an isoelectric focusing. The isoelectric point was determined by running for 2 days at 500V and 4° C. using *AMPHORITE* produced by Amarsham Pharmacia Biotech (pH3.5 to 5.0). In FIG. 8, the solid line represents the absorption of the protein at 280 nm, while ● represents the activity of the α-galactosidase and ◇ represents the pH. As a result, the isoelectric point of this enzyme was 4.2.

Among the characteristics described above, the molecular weight of the α-galactosidase produced by this microorganism determined by the gel filtration method (217,000) and that by the SDS-PAGE (117,000) were larger distinguishably than those of *Aspergillus niger*-produced α-galactosidase reported previously, i.e., 72,000 and 69,000 (both by SDS-PAGE, Enzyme and microbial Technology, 22:383-390, 1998).

EXAMPLE 2

Figure 9:
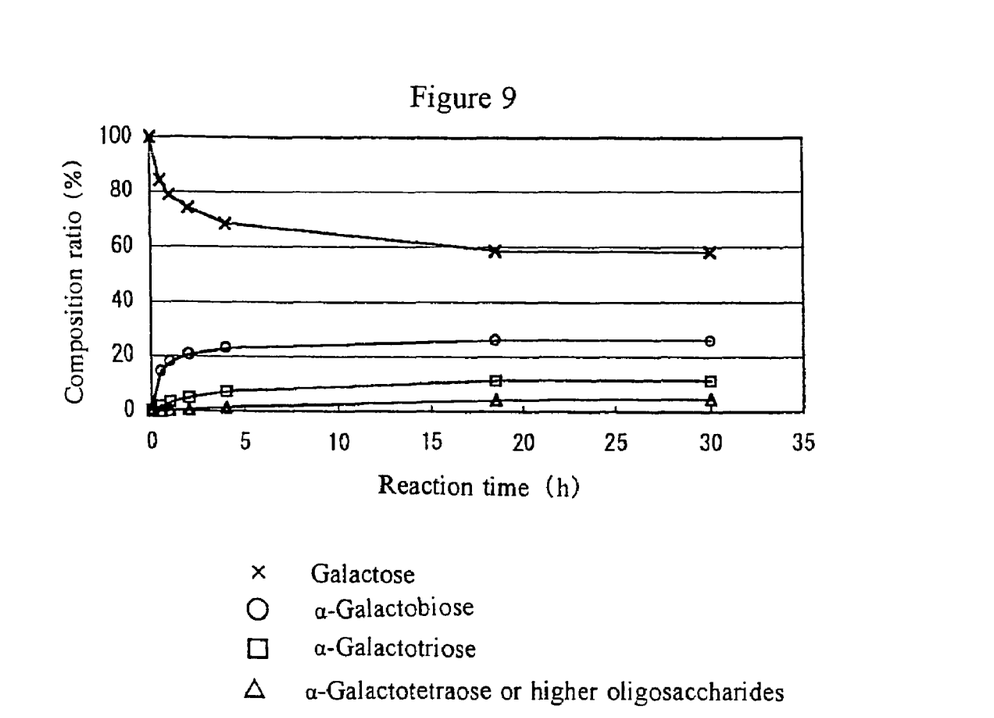
FIG. 9 shows the change with time in the dehydrocondensation reaction starting from galactose in EXAMPLE 2.

Production1 of Oligosaccharide Containing α-galactosyl 100 ml of a buffer solution, pH4.5, containing 60 g of a galactose (WAKO PURE CHEMICAL) and 2,100 U$^M$ of the α-galactosidase obtained in EXAMPLE 1 (galactose concentration: 60% (w/v), enzyme concentration 35 U$^M$-galactose) was prepared, and allowed to react at 50° C. for 30 hours. The change with time during the reaction is shown in FIG. 9.

The reaction solution was loaded onto an activated charcoal column, from which the galactose was eluted with water and the oligosaccharide was eluted with the gradient of ethyl alcohol from 0 to 30%. The eluted oligosaccharide fraction was concentrated into dryness to obtain 24 g of an oligosaccharide containing α-galactosyl. This oligosaccharide produced only galactose when hydrolyzed with an α-galactosidase or an acid.

Figure 10:
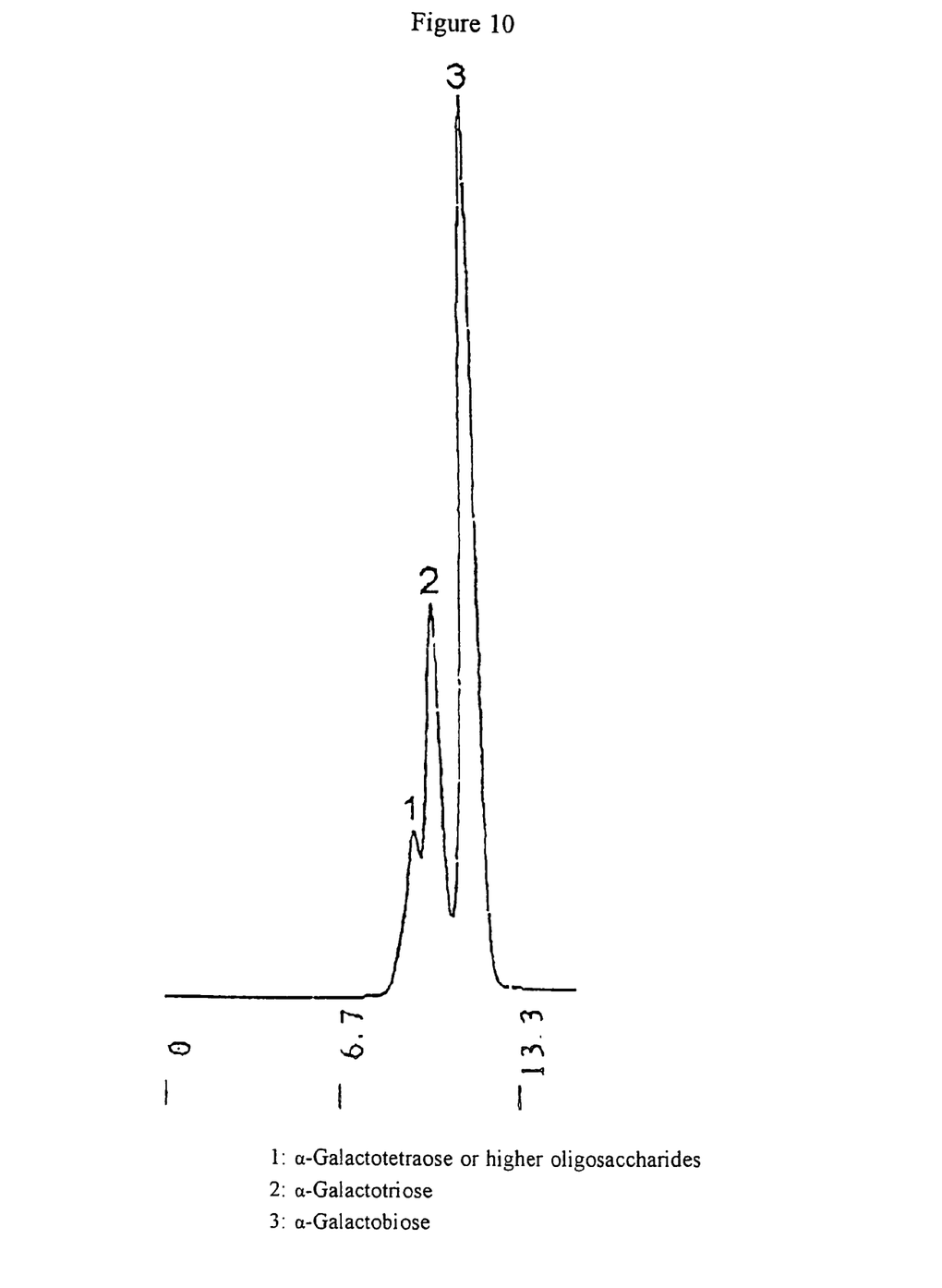
FIG. 10 shows the composition of the oligosaccharide containing α-galactosyl obtained in EXAMPLE 2.

This oligosacchride containing α-galactosyl was subjected to an HPLC analysis (FIG. 10) using a Shim-pack SCR-101 column (SHIMADZU) and revealed to consist of 11% of oligosaccharides of α-galactotetraose or higher saccharides, 27% of α-galactotriose and 62% of α-galactobiose. The reaction product was labeled with an aminobenzoic acid ethyl ester and analyzed on an ODS column, which revealed the binding position isomer composition of the α-galactobiose of α-1,6 bond: α-1,3-bond: α-1,2bond: α-1,4 bond=44:10:5.5: 1.0.

COMPARATIVE 1

Production2 of Oligosacchride Containing α-galactosyl

Using an α-galactosidase produced by *Candida guilliermondii* strain H-404 which is known to have the highest dehydrocondensation reaction-catalyzing activity among the α-galactosidases instead of the α-galactosidase obtained in EXAMPLE 1 and the condition similar to that in EXAMPLE 2, an oligosaccharide was produced.

As a result, it took 90 hours to observe the reaction plateau (vs 30 hours in EXAMPLE 2) in spite of the enzymatic action on melibiose as a substrate similar to that of the α-galactosidase obtained in Example 1, and the yield of the oligosacchride containing α-galactosyl was 14 g (vs 24 g in EXAMPLE 2).

Based on the results described above, the α-galactosidase of the invention obtained in EXAMPLE 1 was proven to have an extremely high enzymatic activity of the dehydrocondensation reaction using a galactose as a substrate, and to be able to produce the oligosaccharide containing α-galactosyl at a high yield within a short period of time.

EXAMPLE 3

Production3 of Oligosacchride Containing α-galactosyl

15 L of a sample containing 9.0 kg of a galactose (WAKO PURE CHEMICAL) and 315,000 $U^M$/g of the α-galactosidase obtained in EXAMPLE 1 (galactose concentration: 60% (w/v), enzyme concentration 35 $U^M$-galactose, pH adjusted at 4.5 with HCl) was prepared, and subjected to a preliminary reaction for 3 hours at 60° C. in a vacuum crystallization container (Crystallization instrument, Model DP, manufactured by TSUKISHIMA KIKAI), and then the reaction solution was concentrated under reduced pressure at 60° C. to 10 L (galactose concentration: 90% (w/v)) and then the concentrate was transferred into a trough crystallization promoter (TSUKISHIMA KIKAI), to which an α-galactosidase whose enzyme concentration was 35 $U^M$/g-galactose was added and the main reaction was effected at 60° C. for 30 hours. The reaction solution was loaded onto an ion exchange column (ligand exchange column having calcium as a ligand), from which the oligosaccharide and the galactose were eluted with water in this order. The eluted oligosaccharide fraction was concentrated into dryness to obtain 5.1 kg of the oligosacchride containing α-galactosyl.

By this production method, the substrate can be used at an extremely high concentration (final concentration: 90%), which promotes the dehydrocondensation reaction of the α-galactosidase extremely, thus enabling an efficient production of an oligosaccharide containing α-galactosyl at a high yield within a short period of time, which is suitable especially for an industrial scale production.

The resultant oligosaccharide containing α-galactosyl produced only galactose when hydrolyzed with an α-galactosidase. This oligosacchride containing α-galactosyl was subjected to an HPLC analysis and revealed to consist of 13% of oligosaccharides of α-galactotetraose or higher saccharides, 31% of α-galactotriose and 56% of α-galactobiose. The binding position of the α-galactosyl group at the reducing terminal was mainly of α-1,6 bond.

EXAMPLE 4

Production4 of Oligosacchride Containing α-galactosyl 100 g of a lactose (WAKO PURE CHEMICAL) was hydrolyzed with a commercially available β-galactosidase (LACTOZYME produced by NOVONORDISC BIOINDUSTRIES) to obtain a mixture of equal amounts of a galactose and a glucose. 100 ml of an acetate buffer, pH4.5, containing 85 g of the equal amount mixture of the galactose and the glucose obtained above and 1,500 $U^M$ of the α-galactosidase obtained in EXAMPLE 1 (saccharide concentration: 85% (w/v), enzyme concentration 35 $U^M$/g-galactose) was prepared, and allowed to react at 50° C. for 87 hours.

Figure 11:
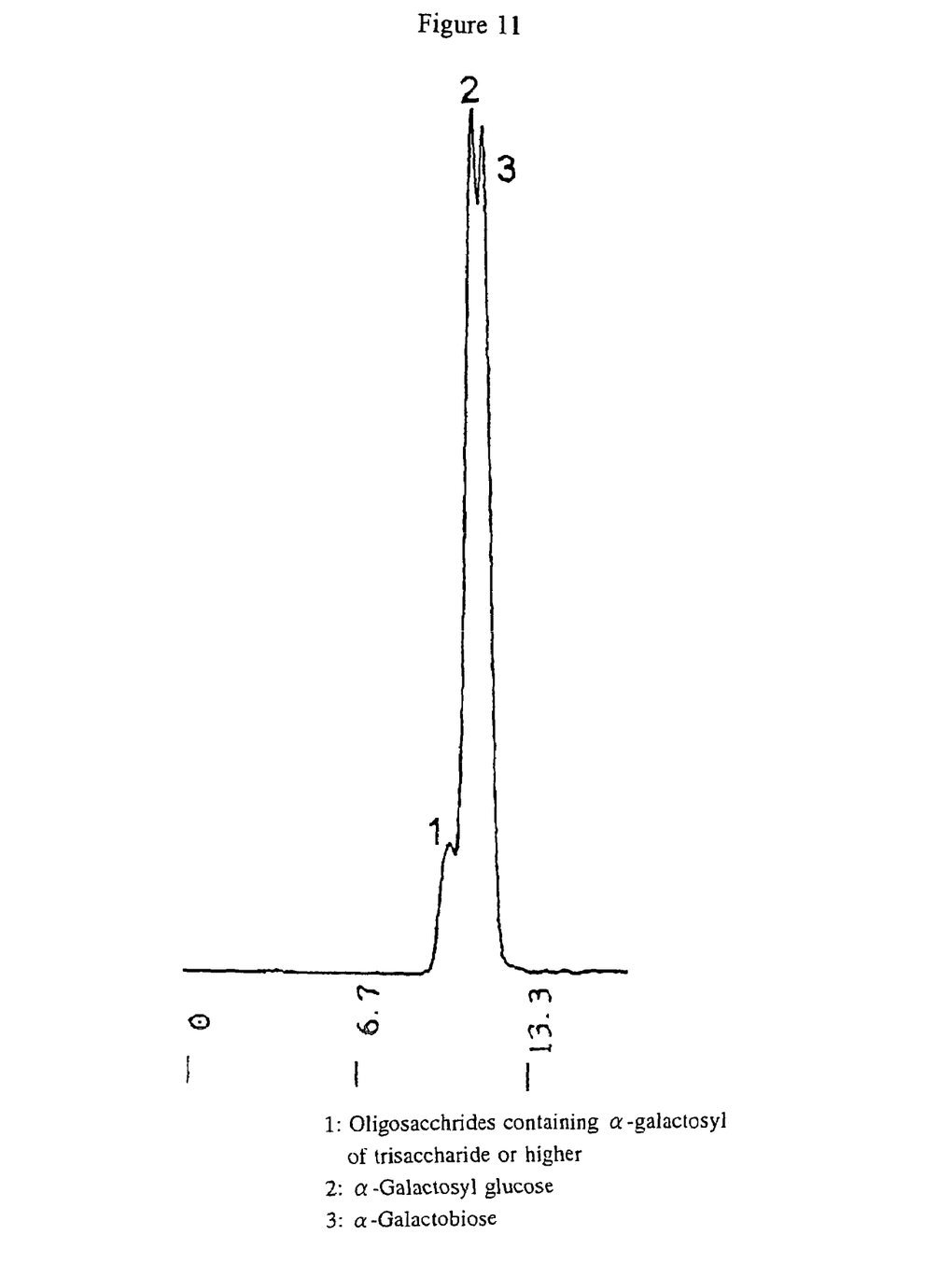
FIG. 11 shows the composition of the oligosaccharide containing α-galactosyl obtained in EXAMPLE 4.

From the reaction solution, 27 g of an oligosacchride containing α-galactosyl was obtained by a column chromatography on an activated charcoal. This oligosaccharide containing α-galactosyl produced only the galactose and the glucose, when hydrolyzed with an acid or α-galactosidase, with the ratio between the galactose and the glucose being about 7:3. This oligosaccharide containing α-galactosyl subjected to an HPLC analysis (FIG. 11) and revealed to consist of 8.0% of trisaccharides or higher oligosaccharides, 48% of α-galactosyl glucose and 44% of α-galactobiose.

COMPARATIVE 2

Production5 of Oligosacchride Containing α-galactosyl

Using an α-galactosidase produced by *Candida guilliermondii* strain H-404 instead of the α-galactosidase obtained in EXAMPLE 1 and the condition similar to that in EXAMPLE 4, an oligosaccharide was produced. As a result, the yield of the oligosacchride containing α-galactosyl was 16 g (vs 27 g in EXAMPLE 4).

Based on the results described above, the α-galactosidase of the invention obtained in EXAMPLE 1 was proven to have an extremely high enzymatic activity of the dehydrocondensation reaction even when using a mixture of the galactose and the glucose as a substrate, and to be able to produce the oligosaccharide containing α-galactosyl at a high yield.

EXAMPLE 5

Figure 12:
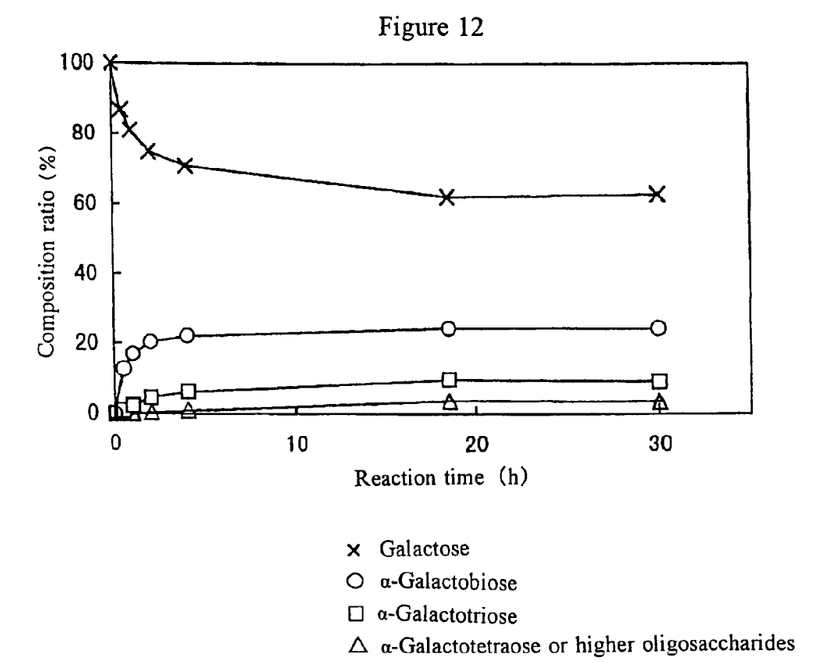
FIG. 12 shows the change with time in the dehydrocondensation reaction starting from galactose in EXAMPLE 5.

Production6 of Oligosacchride Containing α-galactosyl 100 ml of an acetate buffer solution, pH4.5, containing 60 g of a galactose (WAKO PURE CHEMICAL) and 2,100 $U^M$ of an α-galactosidase S-DS derived from *Aspergillus niger* (AMANO ENZYME) (galactose concentration: 60% (w/v), enzyme concentration 35 $U^M$/g-galactose) was prepared, and allowed to react at 50° C. for 30 hours. The change during the reaction is shown in FIG. 12.

The reaction solution was loaded onto an activated charcoal column, from which the galactose was eluted with water and the oligosaccharide was eluted with the gradient of ethyl alcohol from 0 to 30%. The eluted oligosaccharide fraction was concentrated into dryness to obtain 21 g of an oligosacchride containing α-galactosyl. This oligosaccharide produced only galactose when hydrolyzed with an α-galactosidase or an acid. This oligosacchride containing α-galactosyl was subjected to an HPLC analysis and revealed to consist of 9.0% of oligosaccharides of α-galactotetraose or higher saccharides, 25% of α-galactotriose and 66% of α-galactobiose.

EXAMPLE 6

Figure 13:
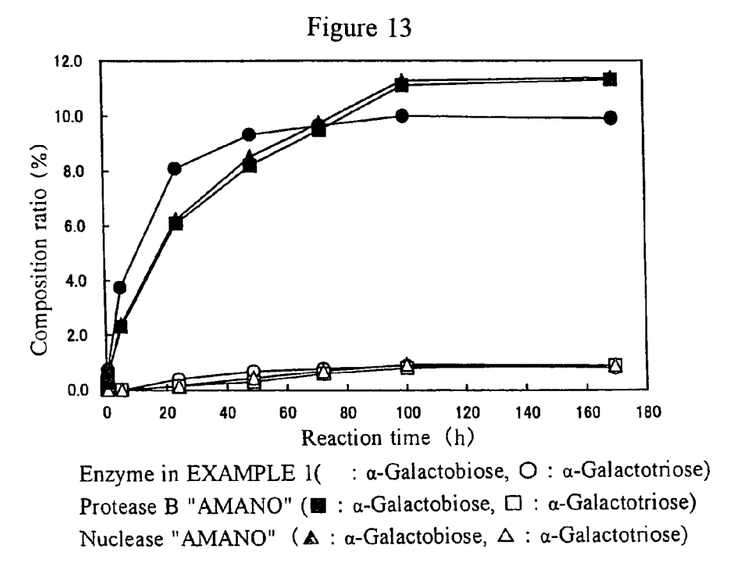
FIG. 13 shows the change in the oligosaccharide employing as a starting material the galactose in EXAMPLE 6.

Production 7,8,9 of Oligosacchride Containing α-galactosyl 100 ml of an acetate buffer, pH4.5, containing 20 g of a galactose (WAKO PURE CHEMICAL) and each 400 $U^M$ of the α-galactosidase obtained in EXAMPLE 1 or the α-galactosidase purified by a known method from *Penicillium citrinum*-derived protease B "AMANO" or nuclease "AMANO" (galactose concentration: 20% (w/v), enzyme concentration 20 $U^M$/g-galactose) was prepared, and allowed to react at 40° C. The change with time during the reaction is shown in FIG. 13.

While the results indicated no difference in the trisaccharide ratio between enzymes, the disaccharide ratios after reaction for 100 hours given by the α-galactosidase obtained in EXAMPLE 1, nuclease "Amano" and protease B "AMANO" were 10.0%, 11.3% and 11.1%, respectively, showing the difference. As evident from these results, there was a difference in the compositions of he galactoses having different binding numbers among the various origins of the α-galactosidase even when the reaction was conducted under the identical condition, and thus the α-galactosidase derived from *Penicillium citrinum* is preferable for the purpose of obtaining an oligosaccharide whose ratio of the disaccharides is high.

EXAMPLE 7

Anti-*Candida* Effect of Oligosacchride Containing α-galactosyl

A *Candida* microorganism was given forcibly via an oral administration to a mouse on diet with the oligosaccharide containing α-galactosyl obtained in EXAMPLE 3 to test the persistence of the *Candida* microorganism in an intestinal tract, whereby assessing the anti-candida effect of the oligosacchride containing α-galactosyl.

(Methods) A test mouse was a 4-week old male mouse of Crj:CD-1 (ICR) line (NIPPON CHARLES RIVER). A preliminary housing was provided to the animal for 1 week while being allowed to access a basal diet and a distilled water ad libitum. The basal diet was a solid chow for mice (MF: ORIENTAL YEAST). After the preliminary housing, the basal diet and the distilled water were given ad libitum continuously, and a control group fed with a sucrose, a positive control group fed with a raffinose, and a treatment group fed with an oligosaccharide containing α-galactosyl were provided (5 animals per group) to conduct a forcible oral administration at 100 mg/animal via an oral gavage for two weeks on a once-a-day basis. One week after initiation of the treatment, the animals in each group received 0.2 ml of a suspension of a *Candida* microorganism (*Candida albicans* IFM40009) prepared at the density of $5.0 \times 10^9$ cells/ml, 1 week after which the cecum and the colon of each mouse were isolated and examined for the viable *Candida* cell count of each organ.

The viable cell of the *Candida* microorganism was counted by applying a *Candida* microorganism suspension diluted appropriately with a physiological saline onto a *Candida* GS (EIKEN KAGAKU) plate medium and incubating at 37° C. for 42 to 48 hours followed by counting the colonies formed. The statistical processing was conducted using a Wilcoxson's rank sum test.

Figure 14:
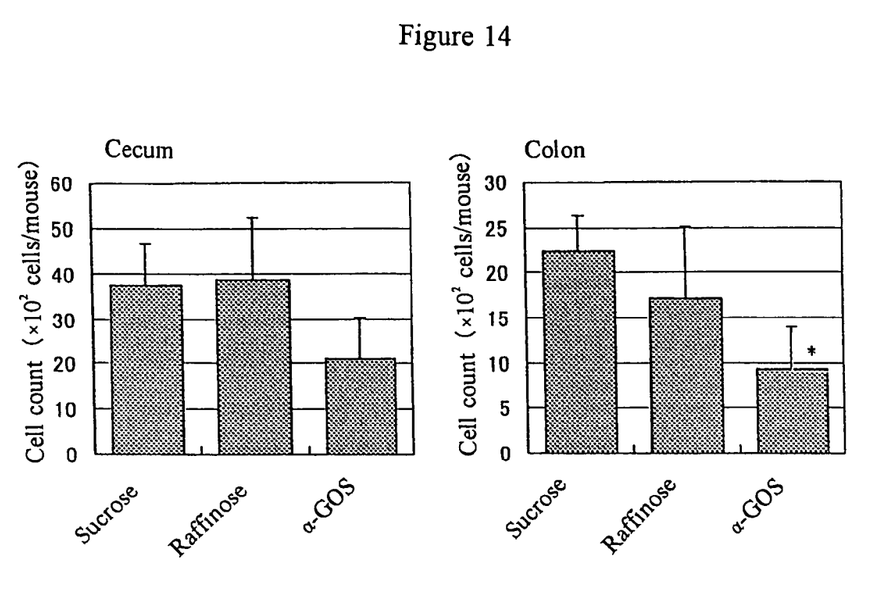
FIG. 14 shows the viable cell counts of a *Candida* microorganism in cecum and various colonic positions. "*" indicates a significant difference observed at a significance level less than 5%.

(Results) The viable cell counts of the cecum and the each part of the colon 1 week after the forcible administration of the *Candida* microorganism suspension are shown in FIG. 14. While the viable cell count of the cecum 1 week after the forcible administration of the *Candida* microorganism suspension was not changed in the control group or the positive control group but was lower in the treatment group, that of the colon was lower in both of the positive control group and the treatment group, with a significantly lower count being observed in the treatment group especially when compared with the control group. In the figure, α-GOS is an oligosacchride containing α-galactosyl.

Based on the results, the oligosaccharide containing α-galactosyl in the treatment group exhibited a potent inhibitory effect on the settlement of the *Candida* microorganism in the intestinal tract, and revealed to have a more excellent anti-candida effect than raffinose.

INDUSTRIAL APPLICABILITY

Since a method of elevating the yield of an oligosaccharide containing α-galactosyl according to the present invention is capable of producing any of various oligosaccharide efficiently at a high yield within a short period of time and is also capable of producing on an industrial scale, it enables a stable and less expensive supply of oligosaccharide.

Also since an anti-candida composition of the invention has an excellent anti-candida effect and can be supplied stably, it can provide a less expensive pharmaceutical or functional food material which enables a safe amelioration or prevention of a *Candida* microorganism-induced mycosis or allergic disease such as an atopic dermatitis.

What is claimed is:

1. A method of producing an oligosaccharide containing an α-galactosyl group comprising the steps of treating galactose or a galactose-containing material with an α-galactosidase derived from *Aspergillus niger* strain APC-9319 (FERM BP-7680), wherein:

a) said α-galactosidase catalyzes the hydrolysis of an α-galactoside bond to liberate D-galactose and the reverse reaction of dehydrocondensation of a free galactose and a compound containing a hydroxyl group to a saccharide containing an α-galactosyl group:

Gal1α-OR+H2O⇌Gal-OH+R—OH wherein Gal1α-OR is a saccharide containing an α-galactosyl group, Gal-OH is a free galactose, and R—OH is a compound containing a hydroxyl group;

b) said α-galactosidase acts on a saccharide having an α-galactosyl group at the non-reducing terminal end of said saccharide;

c) said α-galactosidase has a pH optimum of 2.5 to 6.0; and said α-galactosidase is stable within the range pH 3.5 to 8.0 when allowed to stand for one hour at 40° C.;

d) said α-galactosidase has an optimum temperature of 60° C. at pH 4.5; and said α-galactosidase is stable at a temperature of not greater than 60° C. when allowed to stand at pH 4.5 for 15 minutes;

e) said α-galactosidase has a molecular weight of 217,000 Daltons measured by gel filtration; and said α-galactosidase has a molecular weight of 117,000 Daltons measured by an SDS-PAGE; and f) said α-galactosidase has an isoelectric point of 4.2 measured by isoelectric focusing; and recovering the oligosaccharide containing the α-galactosyl group.

2. A method of producing an oligosaccharide containing an α-galactosyl group comprising the steps of treating galactose or a galactose-containing material with an α-galactosidase derived from *Aspergillus niger* strain APC-9319 (FERM BP-7680), wherein:

a) said α-galactosidase catalyzes the hydrolysis of an α-galactoside bond to liberate D-galactose and the reverse reaction of dehydrocondensation of a free galactose and a compound containing a hydroxyl group to a saccharide containing an α-galactosyl group:

Gal1α-OR+H20⇌Gal-OH+R—OH wherein Gal1α-OR is a saccharide containing an α-galactosyl group, Gal-OH is a free galactose, and R—OH is a compound containing a hydroxyl group;

b) said α-galactosidase acts on a saccharide having an α-galactosyl group at the non-reducing terminal end of said saccharide;

c) said α-galactosidase has a pH optimum of 2.5 to 6.0; and said α-galactosidase is stable within the range pH 3.5 to 8.0 when allowed to stand for 1 hour at 40° C.;

d) said α-galactosidase has an optimum temperature of 60° C. at pH 4.5; and said α-galactosidase is stable at a temperature of not greater than 60° C. when allowed to stand at pH 4.5 for 15 minutes;

e) said α-galactosidase has a molecular weight of 217,000 Daltons measured by gel filtration; and said α-galactosidase has a molecular weight of 117,000 Daltons measured by an SDS-PAGE; and f) said α-galactosidase has an isoelectric point of 4.2 measured by isoelectric focusing; and wherein said method further comprises the steps of treating said galactose or said galactose-containing material with said α-galactosidase to effect a preliminary dehydrocondensation reaction to produce an initial amount of a reaction solution comprising an oligosaccharide containing an α-galactosyl group followed by concentrating said reaction solution under reduced pressure to produce a higher concentration of galactose than was originally present and then effecting a subsequent dehydrocondensation reaction to further elevate the yield of oligosaccharide containing the α-galactosyl group; and recovering the oligosaccharide containing the α-galactosyl group.

3. A method of producing an oligosaccharide containing an α-galactosyl group comprising treating galactose or a galactose-containing material with an α-galactosidase obtained from *Aspergillus niger* strain APC-9319 (FERM BP-7680) to effect a preliminary dehydrocondensation reaction to produce an initial amount of an oligosaccharide containing an α-galactosyl group followed by concentrating said reaction solution under reduced pressure to produce a higher concentration of galactose than was originally present and then effecting a subsequent dehydrocondensation reaction to further elevate the yield of the oligosaccharide containing the α-galactosyl group and recovering the oligosaccharide containing the α-galactosyl group.

4. A method of producing an oligosaccharide containing an α-galactosyl group comprising treating galactose or a galactose-containing material with an α-galactosidase obtained from *Aspergillus niger* strain APC-9319 (FERM BP-7680) and recovering the oligosaccharide containing the α-galactosyl group.

* * * * *